US006407373B1

(12) United States Patent
Dotan

(10) Patent No.: US 6,407,373 B1
(45) Date of Patent: Jun. 18, 2002

(54) APPARATUS AND METHOD FOR REVIEWING DEFECTS ON AN OBJECT

(75) Inventor: Noam Dotan, Givaataim (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 09/334,115

(22) Filed: Jun. 15, 1999

(51) Int. Cl.$^7$ ............................................. G02B 27/40
(52) U.S. Cl. ................................................. 250/201.3
(58) Field of Search ............................ 250/200, 201.1, 250/201.2, 201.3, 201.4; 356/237.2, 237.3, 237.4, 237.5

(56) References Cited

U.S. PATENT DOCUMENTS

| | | | |
|---|---|---|---|
| 4,598,997 A | 7/1986 | Steigmeier et al. | 356/237 |
| 4,898,471 A | 2/1990 | Stonestrom et al. | 356/394 |
| 5,216,235 A | 6/1993 | Lin | 250/201.6 |
| 5,267,017 A | 11/1993 | Uritsky et al. | 356/375 |
| 5,479,252 A * | 12/1995 | Worster et al. | 356/237 |
| 5,497,007 A | 3/1996 | Uritsky et al. | 250/491.1 |
| 5,659,172 A | 8/1997 | Wagner et al. | 250/307 |
| 5,734,164 A | 3/1998 | Sanford | 250/310 |
| 5,917,588 A * | 6/1999 | Addiego | 356/237 |
| 6,011,619 A * | 1/2000 | Steffan et al. | 356/237.3 |
| 6,067,154 A * | 5/2000 | Hossain et al. | 356/237.2 |

FOREIGN PATENT DOCUMENTS

EP   WO97/33158   5/1997

* cited by examiner

Primary Examiner—Frank G. Font
Assistant Examiner—Michael P. Stafira
(74) Attorney, Agent, or Firm—McDermott, Will & Emery

(57) ABSTRACT

An apparatus and method are disclosed for reviewing defects on an object. The apparatus includes a stage for receiving the object thereon, and both an optical microscope and a scanning electron microscope (SEM). The optical microscope is used to redetect previously mapped defects on the object surface, and includes an illumination source that directs a beam of light toward a selected portion of the object surface. The optical microscope is configured to generate either, or both, bright field and dark field illumination. Once the defect has been redetected, a translation system moves the stage a predetermined displacement such that the defect is positioned for review by the SEM. The apparatus can be configured to automatically focus the defect for viewing by the SEM, and rotate the stage to obtain varying perspectives of the defect.

26 Claims, 7 Drawing Sheets

APPARATUS AND METHOD FOR REVIEWING DEFECTS ON AN OBJECT

BACKGROUND OF THE INVENTION

1. Field of the Invention

The present invention relates to defect review systems, and ore particularly, to an apparatus and method for redetecting and classifying defects that exist on an object.

2. Description of the Invention

Microelectronic devices are typically fabricated, in part, by forming features (e.g., patterns) on selected layers of a semiconductor wafer. The escalating requirement for high density performance associated with ultra large scale integration (ULSI) semiconductor devices requires design features of sub 0.25 micron, increased transistor and circuit speeds, high reliability, and increased manufacturing throughput for competitiveness. The reduction of design features to 0.18 micron and under challenges the limitations of conventional semiconductor manufacturing techniques. Moreover, as design features are reduced into the deep sub-micron range, it becomes increasingly difficult to maintain or improve manufacturing throughput, (i.e., production yield) for competitiveness.

One factor that affects manufacturing throughput is the presence of defects on the semiconductor wafer during the manufacturing process. Defects can take various forms, such as, for example, scratches, particles, and unremoved portions of material layers on the surface of the semiconductor wafer. Undetected defects can often lead to failure of a semiconductor chip that is made from the wafer.

An in-line inspection and review is normally performed to detect and to classify defects that are detected on the semiconductor wafer during the manufacturing process. Classification of defects on the semiconductor wafer involves, among other things, the ability to extract accurate information such as defect size, shape, and boundary in order to identify the sources of the defects. This operation requires very high resolution imaging. As features on the semiconductor wafers become smaller, however, the size of the defects that can affect production yield falls below the resolution of conventional light optics. Therefore, the ability to classify defects using optical systems is becoming highly limited. Accordingly, there is an increasing need for higher resolution systems for defect classification.

The Scanning Electron Microscope (SEM) is capable of resolving features with a size of a few nanometers and, when combined with analytical tools such as Energy is Dispersive X-ray Spectrum (EDX), is a natural candidate for carrying out the defect classification on semiconductor wafers. Generally, an inspection system is used to scan the semiconductor wafer and generate a defect map of locations on the semiconductor wafer suspected of having defects thereupon. The defect map is then transferred to the SEM to acquire high-resolution images of each defect. The defect maps generated by inspection tools suffers from low accuracy, relative to the size of the defects. Hence, the SEM must "redetect" (i.e., re-find) the defects, before generating the high resolution image required for classification. Specifically, the accuracy of the inspection tool is sufficient for detecting the presence of the defect, but insufficient for accurately determining the location of the defect. The defect map generated by the inspection tool is therefore unable to guide the SEM to the exact location of the defect. Accordingly, redetection functions as a bridge between the optical inspection tool's output and the ability of the SEM to satisfy the demand for high resolution imaging of the defect for classification purposes. Of course, the smaller the defect, the smaller the field of view of the image and thus, a more accurate location of the defect must be known in order to redetect the defect. Moreover, when EDX or Auger analysis is performed, the required accuracy must be better than the defect's size.

Unfortunately, due to conflicts between high sensitivity and fast operation of the optical inspection tool, defect maps of the optical inspection tools are not sufficiently accurate for fast redetection by the SEM. Specifically, systematic errors are introduced due to inaccuracy in various system components or inaccuracy in aligning the wafer. Even after minimizing the systematic error, there is a relatively large degree of uncertainty in the reported defect locations (i.e., defect map) due to the inspection is system's settings. For example, in order to increase the throughput of the inspection system, the spot size used to scan the semiconductor wafer is normally selected to be much larger than the defects' size. Thus, the reported coordinates of the spot size location encompass an area that is much larger than the location of the defect.

For example, uncorrected position error caused by settings of the spot size can be in the order of $\pm 10\mu$ for patterned wafers, and may exceed $\pm 50\mu$ for unpatterned wafers. The magnitude of this error unacceptably increases the search window size for the SEM in order to redetect the defect. For example, detection of a $0.2\mu$, defect in a field of view of $20\mu$ results in an image of 5×5 image pixels for the defect (at 500×500 pixels in image). This is a very severe requirement for SEM based detection systems due to low contrast to noise ratio generally achieved in SEM imaging. Consequently, while a reliable SEM redetection system, such as described in U.S. Pat. No. 5,659,172, may be used to find the defect, it can take an unacceptably long period of time, hence resulting in reduced throughput for the system.

Moreover, SEM-based redetection is ineffective for defects buried under (or within) an optically transparent layer. Consequently, it may be impossible to obtain a SEM image of the buried defect with sufficiently clear details to facilitate classification. Further, small variations in layer thickness are often reported as defects by inspection systems, but generally very difficult to redetect using SEM. Therefore, such a defect may not be classifiable using the SEM image.

Accordingly, one problem associated with current methods of reviewing defects on materials such as semiconductor wafers, is the inability for SEM-based review tools to quickly and accurately redetect the defects based on a defect map generated by an inspection tool. Another problem associated with current methods of reviewing defects is the unavailability of supplemental systems to assist in classifying defects when the SEM-based image is not amenable to classification.

SUMMARY OF THE INVENTION

There exists a need for an arrangement that is capable of quickly and accurately redetecting defects on materials such as semiconductor wafers. There also exists a need for an arrangement that is capable of classifying defects that are not detectable by an SEM.

These and other needs are addressed by the present invention wherein a defect review system includes both an optical microscope and an SEM, thereby allowing quick and accurate redetection and classification of anomalies such as defects. Specifically, the optical system can be used to redetect a defect reported in a defect map. The optical system can also be used to obtain a highly magnified images of the defects in cases where the SEM cannot obtain an image (e.g., defect buried in a transparent dielectric layer).

In accordance with one aspect of the present invention, an apparatus is provided for reviewing defects on an object's surface, based on a previously generated defect map. The apparatus comprises a stage, an optical microscope, an imaging unit, a particle beam imaging system, and a translation system. The stage functions as a platform upon which the object may be placed. The optical microscope includes an illumination source that directs a beam of light toward a selected portion of the object surface along an illumination path. The optical microscope is used to redetect the defects on the object surface based on information contained in the defect map. The imaging unit is coupled to the optical microscope and generates an image of the selected portion of the object surface. The particle beam imaging system converges a beam of particles, along a prescribed axis, to a focal point. The translation system moves the stage a predetermined displacement such that the redetected defect will be positioned proximate the focal point. The defect can then be reviewed by the particle beam imaging system.

According to one specific embodiment of the present invention, the optical microscope is configured to selectively provide different types of illumination. For example, the selected portion of the wafer can be examined under a bright field illumination, dark field illumination, or both. Hence, defect redetection can be improved by utilizing an illumination type which is most similar to the illumination type used by the inspection microscope to construct the defect map.

According to another specific embodiment of the present invention, an optical redetection and review system is configured together with an optical focusing system. Specific optics are provided to allow automatic autofocusing, optical redetection, and optical review.

In accordance with another aspect of the present invention, a method for reviewing defects on an object surface, based on a previously generated defect map, comprises the steps: viewing selected portions of the object surface, based on coordinates from a defect map, to redetect the defects; determining stage coordinates corresponding to the location of the redetected defects; moving the object surface to position the redetected defects proximate a focal point of a particle beam imaging system; and reviewing the redetected defects using the particle beam imaging system.

Additional advantages and novel features of the present invention will be set forth in part in the description which follows, and in part will become apparent to those skilled in the art upon examination of the following, or may be learned by practice of the invention. The advantages of the invention may be realized and attained by means of the instrumentalities and combinations particularly pointed out in the appended claims.

BRIEF DESCRIPTION OF THE DRAWINGS

Reference is made to the attached drawings, wherein elements having the same reference numeral designations represent like elements throughout and wherein.

DETAILED DESCRIPTION OF ILLUSTRATIVE EMBODIMENTS

The present invention will be described with reference to examples of semiconductor wafer review systems, and, in particular, the review systems used to redetect and examine defects. It will become apparent, however, that the present invention is also applicable to other systems used to inspect materials such as photomasks, magnetic disks, optical disks, mirrors, etc.

Figure 1:
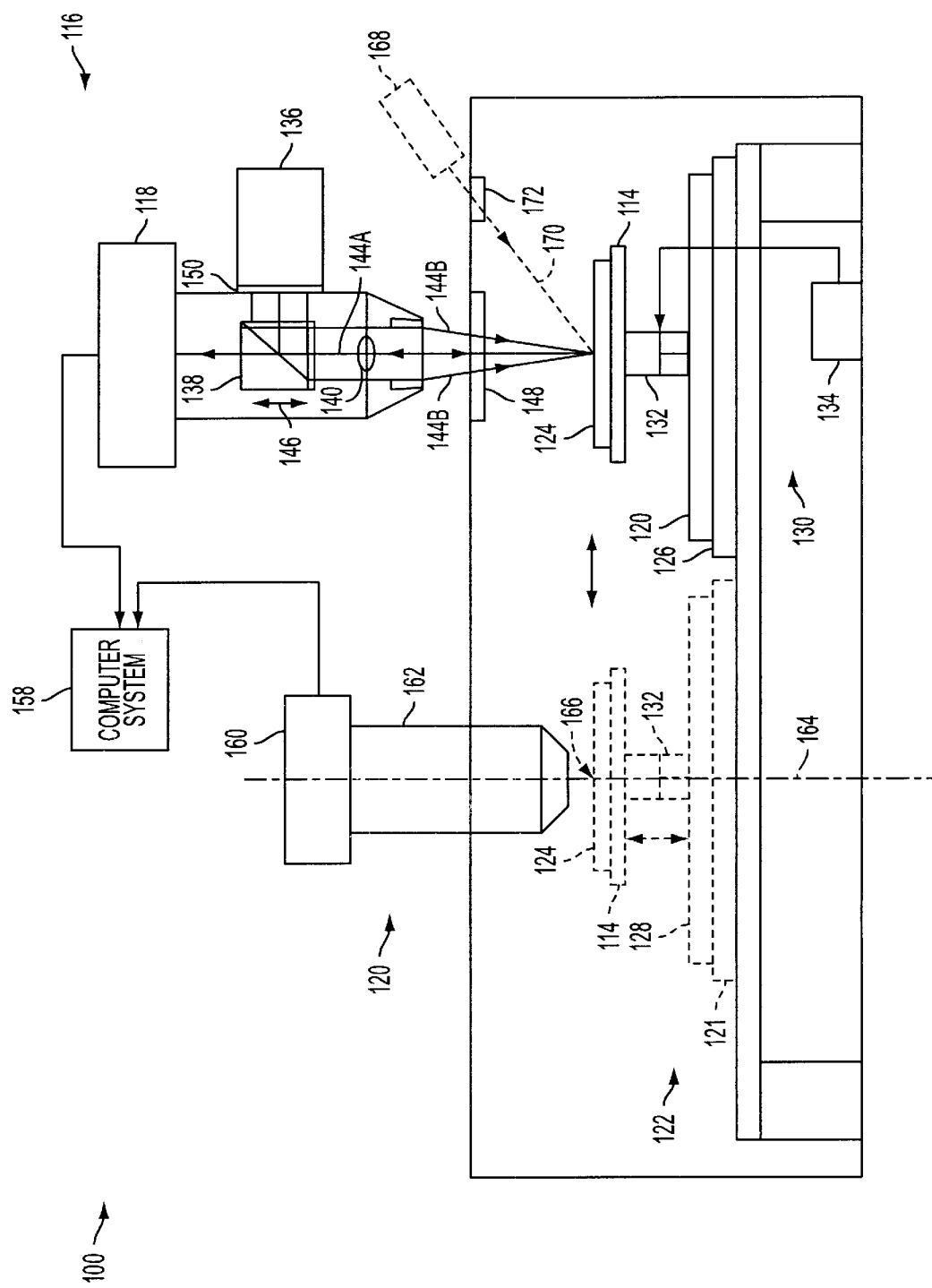
FIG. 1 is a side elevational view of a wafer inspection system constructed in accordance with an exemplary embodiment of the present invention.

FIG. 1 is a side elevational view of a wafer review system 100 constructed in accordance with an exemplary embodiment of the present invention. The wafer review system 100 of FIG. 1 includes a vacuum chamber 112 that houses a stage 114 coupled to a translation system 122. An optical microscope 116 provides optical images via window 148 in vacuum chamber 112, and a particle beam imaging system 120 provides particle beam-based images of objects placed in the vacuum chamber 112.

The stage 114 is configured as a platform upon which an object such as, for example, semiconductor wafer 124 may be placed. The translation system 122 includes a first motorized base 126 for adjusting the position of the semiconductor wafer 124 along a first axis, such as an X-axis. The translation system 122 also includes a second motorized base 128 for adjusting the position of the semiconductor wafer 124 along a second axis, such as a Y-axis. The first and second motorized bases 126, 128 can be controlled for operation along predetermined paths using various types of drive systems, such as, for example, electric motors (not shown). Accordingly, the semiconductor wafer 124 positioned on the stage 114 is movable along a plane defined by the X and Y-axes. As is known in the art, the stage 114 can also include an appropriate locking unit (not shown) for securing the semiconductor wafer 124 in a preset orientation.

The wafer review system 100 can include a vertical displacement unit 130 for adjusting the vertical position of the stage 114. The vertical displacement unit 130 can include, for example, a lift 132 that is operated by a motor 134. Further, multiple vertical displacement unit 130 can be used, and, in such circumstances, circuitry can be provided to synchronize operation of the motors 134 so that the X-Y plane remains substantially flat during adjustments along the Z-axis. The vertical displacement unit 130 can also function to assist in focusing images of the semiconductor wafer 124 when viewed by either the optical microscope 116 or the SEM 120. Of course, various other methods for focusing such as, for example, changing the voltage in the electron column or manipulating the objectives and/or other optical elements, can be used.

The optical microscope 116 includes an illumination source 136, a semi-reflective mirror 138, a lens 140, and a deflection mirror 142. The illumination source 136 can, for example, be in the form of a Kohler type illumination lamp capable of producing a beam 144 of fixed or variable spot size, as described in *Principles of Optics*, by Max Born and Emil Wolf, Pergamon Press, 1980. The illumination can also be in the form of a laser capable of producing a beam 144 of fixed or variable spot size. Alternatively, a beam expander (not shown) can be used to increase the spot size of the beam 144. The semi-reflective mirror 138 is positioned such that the beam 144 output by the illumination source 136 strikes the surface thereof and is reflected along an illumination path 146 that is substantially perpendicular to the X-Y plane. As illustrated in FIG. 1, the wafer review system 100 can include a first optical window 148 through which the semiconductor wafer 124 can be viewed by the optical microscope 116 (e.g., if the optical microscope 116 is positioned outside of the vacuum chamber 112). Alternatively, the optical microscope 116 can extend into the vacuum chamber 112.

Figure 2:
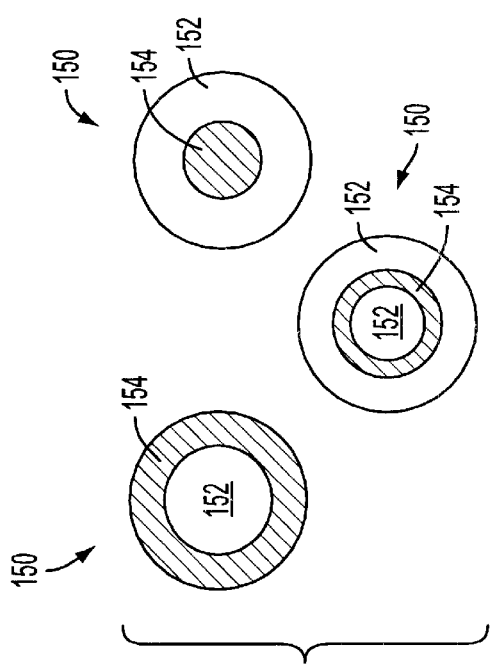
FIG. 2 is a block diagram illustrating the various configurations of a light field selector according to an embodiment of the present invention.

According to the disclosed embodiment of the present invention, the illumination source 136 is provided with a light field selector 150 that allows selection of various types of light fields such as, for example, bright field illumination, dark field illumination, or both. Referring additionally to FIG. 2, the various operating configurations of the light field selector 150 are illustrated. The light field selector 150 can include various geometric areas of transparent and opaque regions 152, 154. Each configuration of the light field selector 150 results in a specific type of light field. For example, if the outer portion of the light field selector 150 is opaque, then a first beam 144A will pass through the center of the light field selector 150 and cause a bright field illumination. If the central portion of the light field selector 150 is opaque, a second beam 144B will pass through the periphery of the light field selector 150 and generate a dark field illumination. Alternatively, the light field selector 150 can include an annular, opaque portion disposed between transparent regions to form a combination of bright field or dark field illumination.

Alternatively, the light field selector 150 can be implemented in various other ways. For example, multiple disks can be physically placed in front of the beam 144 to allow passage of prescribed light patterns. Further, the light field selector 150 can include regions of different color filters instead of transparent and opaque regions 152, 154. For example, region 152 can be configured as a first color filter such as, for example, a blue and green filter. Next, region 154 can be configured as a second color filter such as, for example, a red filter. Also, rather than incorporating regions of different colors, the light field selector 150 can be in the form of a polarizing filter wherein regions 152 and 154 are configured to polarize the beam 144 output by the illumination source 136. Filters can often prove beneficial in resolving images when both bright field illumination and dark field illumination are used simultaneously.

As illustrated in FIG. 1, when bright field illumination is used, the first beam 144A reflects from the semi-reflective mirror 138 and passes through the lens 140, where it is focused on the surface of the semiconductor wafer 124. When dark field illumination is used, the second beam 144B reflects from the semi-reflective mirror 138 and passes around the lens 140. The deflection mirror 142 is positioned within the conical portion of the optical microscope 116 such that it reflects the second beam 144B toward the surface of the semiconductor wafer 124 at an oblique angle. Alternatively, the focusing mirror 142 can be parabolically shaped in order to focus the beam 144 onto a focus on the selected area of the semiconductor wafer. The oblique angle is typically chosen so that no specularly reflected light would enter the lens 140. FIG. 1 is intended to illustrate operation of the present invention, and therefore does not accurately reproduce the geometric orientation of the oblique angle.

During bright field illumination, the first beam 144A strikes the surface of the semiconductor wafer 124, and is reflected back toward the lens 140 along the illumination path 146. The reflected first beam 144A passes through the semi-reflective mirror 138 and is received by an imaging unit 118 such as, for example, a Charge Coupled Device (CCD). The imaging unit 118 collects the first beam 144A and generates a bright field image representative of the selected portion of the semiconductor wafer 124.

During dark field illumination, however, the oblique angle of the second beam 144B normally results in a reflected second beam 144B that will not pass through the lens 140 of the wafer review system 100. However, any particles that are present on the surface of the semiconductor wafer 124, or buried beneath a transparent deposited layer, will cause the second beam 144B to scatter and be reflected toward the lens 140. The reflected second beam 144B is collimated by the lens 140 and passed through the semi-reflective mirror 138. The imaging unit 118 also collects the second beam 144B and generates a dark field representation of the selected portion of the semiconductor wafer 124.

The imaging unit 118 can include filters 156 (not shown) for filtering the images. In particular, the filters included in the imaging unit 118 correspond to, for example, the polarizing filters used in the light field selector 150, if and when such filters are used. For example, when a particular polarizing filter type is used to generate the first beam 144A, a similar polarizing filter is used by the imaging unit 118 to develop the bright field image. Similarly, when a particular polarizing filter type is used to generate the second beam 144B, a corresponding polarizing filter is used by the imaging unit to develop the dark field image. If the light field selector 150 is in the form of color filters, then the imaging unit 118 is preferably selected to be a color CCD. Since conventional color CCD provides separate outputs for blue, green and red, it can inherently perform the filtering operation. For example, if the bright field filter of the illumination selector 150 is green/blue and dark field filter is red, then the green/blue output of the CCD would produce the bright field image, while the red output of the CCD would produce the dark field image. As previously stated, the use of filters facilitates resolving images using both bright field and dark field illumination.

As illustrated in FIG. 1, the wafer review system 100 also includes a particle beam imaging system such as the scanning electron microscope (SEM) 120. SEMs and their use in high resolution imaging are well known, and as such, will not be described in great detail. The SEM 120 includes an electron gun 160 and an electron optical column 162 having, for example, a low chromatic conical objective lens (not shown) of approximately 60°. The electron gun 160 and the electron optical column 162 form a beam of particles (i.e., electrons). The beam of electrons is directed along an electron beam axis 164 and converged to a focal point 166. The electrons are generally directed at a sample being examined such that they penetrate the sample, and generate secondary and back-scattered electrons. Detectors (not shown) are then used to collect the secondary and back-scattered electrons to generate an image of the sample.

The wafer review system 100 illustrated in FIG. 1 greatly simplifies the review process used to identify and classify defects that have been previously mapped for a semiconductor wafer 124. For example, during the inspection process, an inspection microscope is used to quickly identify potential defects on a semiconductor wafer 124 and generate a wafer defect map. The inspection microscope must be optimized both for speed and detection sensitivity. Consequently, a relatively low resolution (i.e., large pixel size or beam width) must be used. The resulting defect map contains a list of coordinates for identification of the location of potential defects. However, the precision with which the coordinates of the potential defects are mapped is not very accurate because of the large field of view used to quickly scan the semiconductor wafer 124. For example, when a defect is located using a large spot size, the defect cannot be easily redetected because it is not known where, within the spot size, the defect is actually located. In essence, the defect maps generated by conventional wafer inspection systems map the coordinates of the spot used to scan the semiconductor wafer 124. Accordingly, it is difficult to quickly redetect the defects using a review tool that only utilizes an SEM. SEM imaging systems, however, suffer from very low contrast to noise ratio. Therefore when a large field of view, that reflects the existing inaccuracy in defect location, is used, small defects will be barely detected.

According to the embodiment of the present invention illustrated in FIG. 1, a semiconductor wafer 124 that has been previously inspected for generation of a defect map is placed on the stage 114 and first examined using the optical microscope 116. The optical microscope 116 receives coordinates corresponding to the location of potential defects and examines such locations to verify the existence of the defect. According to such a procedure, only areas that contain potential defects are examined. Preferably, the optical microscope 116 utilizes an illumination type that is similar to the illumination type used during the inspection process that generates the defect map. For example, most defect maps are generated using an inspection microscope that employs dark field illumination. Consequently, the use of dark field illumination in the optical microscope 116 of the wafer review system 100 of the present invention increases the probability that potential defects from the defect map will be redetected. The optical microscope 116 of the present invention preferably includes a significantly higher resolution than the inspection microscope used to generate the defect map. Hence, once a defect is identified, accurate coordinates can be determined for the wafer review system 100.

As previously stated, the stage of the present wafer review system 100 includes first and second motorized bases 126, 128 that function to move the stage along the X and Y axes, respectively. Accordingly, once a defect has been located using the optical microscope 116 and accurate coordinates have been determined for its location, such coordinates are used to control movement of the first and second motorized bases 126, 128 to align the semiconductor wafer 124 with the optical axis 164 of the SEM 120. Since the optical microscope 116 has a higher resolution than the inspection microscope, the accuracy with which the defect is positioned relative to the optical axis 164 of the SEM is greatly improved. With such an improvement, the defect will normally be positioned within the field of view of the SEM 120, hence eliminating the need for an expanded search of the semiconductor wafer 124 in order to locate the defect.

According to one embodiment of the present invention, the illumination source 136 used in the optical microscope 116 is configured to produce only a beam 144 for generating bright field illumination. According to such an embodiment, a light field selector 150 would normally be in the form of a polarizer or color filter. Alternatively, a laser having a prescribed spot size for generating bright field illumination can be used. Next, a second illumination source 168, such as a laser, is disposed outside the vacuum chamber 112 of the wafer review system 100. The second illumination source 168 is positioned to direct an auxiliary beam 170 at the selected portion of the semiconductor wafer 124 through an auxiliary window 172. Further, the auxiliary beam 170 is directed at an oblique angle, as previously described. Such an arrangement further eliminates the need for a deflection mirror 142 to direct the second beam 144B from the first illumination source 136 onto the selected portion of the semiconductor wafer 124. When the auxiliary beam 170 from the second illumination source 168 strikes the surface of the semiconductor wafer 124 it is normally reflected and does not pass through the optical window 148. As previously described, however, the presence of any particles on or near the surface of the semiconductor wafer 124 will result in scattered light that is reflected back to the lens 140 and imaged by the imaging unit 118. The second illumination source 168 can also be a plurality of light sources that help to achieve two targets. First, the amount of scatter light from small particles can be increased. Second, the plurality of light sources can filter out directional scatter from large metal grains on a deposition layer (which are not defects), that are mainly scattering light to one direction while the light scatter from small defect is usually scattered more uniformly. By comparing the image generated from different illumination direction, the grains can be substantially filtered. These light sources can be either switched one at a time or be of different colors. As with the previous example, the light provided from the first and second illumination sources 136, 168 can be given different characteristics to allow distinction between bright and dark field images. For example, if the light from the first illumination source 136 is filtered to blue/green and the light from source 168 is red, then the various color outputs of a CCD can be used to obtain bright and dark field images simultaneously.

Figure 3:
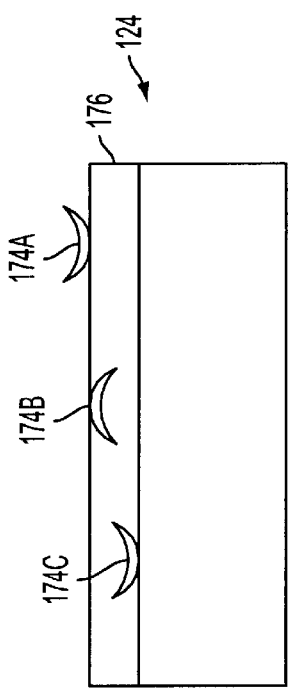
FIG. 3 is a side elevational view of a semiconductor wafer, illustrating various types of defects.

The wafer review system 100 of the present invention also increases the ability to detect particles that are buried within, or beneath, a transparent dielectric layer of the semiconductor wafer 124, such as a CMP layer. FIG. 3 illustrates a portion of a semiconductor wafer 124 and exemplary locations of particles 174. The semiconductor wafer 124 contains a layer 176 that has been formed thereon using an appropriate technique such as deposition. As illustrated in FIG. 3, particles 174 can be found at various locations on the semiconductor wafer 124. Specifically, particle 174A is positioned on the surface of the layer 176, particle 174B is trapped within the layer 176, and particle 174C is trapped beneath the layer 176.

It is well known that SEMs 120 are unable to detect particles 174 that are buried deep beneath a surface that may be transparent to light-based optical systems. Furthermore, there are various other types of defects that are difficult to classify using an SEM 120. For example, variations in layer thickness can often be reported as a defect. Also, large defects that exceed the spot size of the electron beam used by the SEM 120 cannot be detected. The aforementioned defect types, however, are detectable using an optical review system.

According to the disclosed embodiment of the present invention, when the optical microscope 116 locates a defect on the surface of the semiconductor wafer 124, the same defect will be subsequently examined, and possibly classified, by the SEM 120. If the SEM 120 is unable to locate a defect within the vicinity of the coordinates reported by the optical microscope 116, the defect is again examined using the optical microscope 116. If, for example, examination of the region using dark field illumination verifies the presence of the defect, then a bright field illumination can be used under high magnification to view the defect and confirm that the defect is in the form of a particle 174 buried beneath the surface of the semiconductor wafer 124.

Although the advantages of combining an optical microscope with a particle beam imaging system have been described with respect to redetection of the defects, it should be appreciated that numerous additional advantages can be gained. For example, the arrangement of the present invention is also advantageous for defect classification. Specifically, SEM review systems, such as the SEM Vision available from Applied Materials of Santa Clara, Calif., review located defects and classify them into particular defect classes. In the SEMVision the image obtained by the electron column is analyzed in a computer system to determine prescribed defect classes. However, as noted previously, when the defect is buried in a layer, such as a CMP layer, it may be difficult to classify the defect using the SEM-based image. Similarly, small variations in thickness, that are difficult to classify using a SEM-based image, can appear as color variations in an optical image.

Therefore, according to one embodiment of the present invention, a computer system 158 is coupled to the SEM 120, as is done in the SEMVision, and also to the imaging unit 118 (as illustrated in FIG. 1). The computer system 158 uses the optical images for automatically examining defects that are not visible to the electron-based imaging unit 120. According to such an embodiment, the imaging unit 118 converts the resolved image into digital data (i.e., a digital image) that is transferred to the computer system 158. The computer system 158 examines the digital image and analyzes its characteristics so as to assign the defect to a particular defect class.

Figure 4:
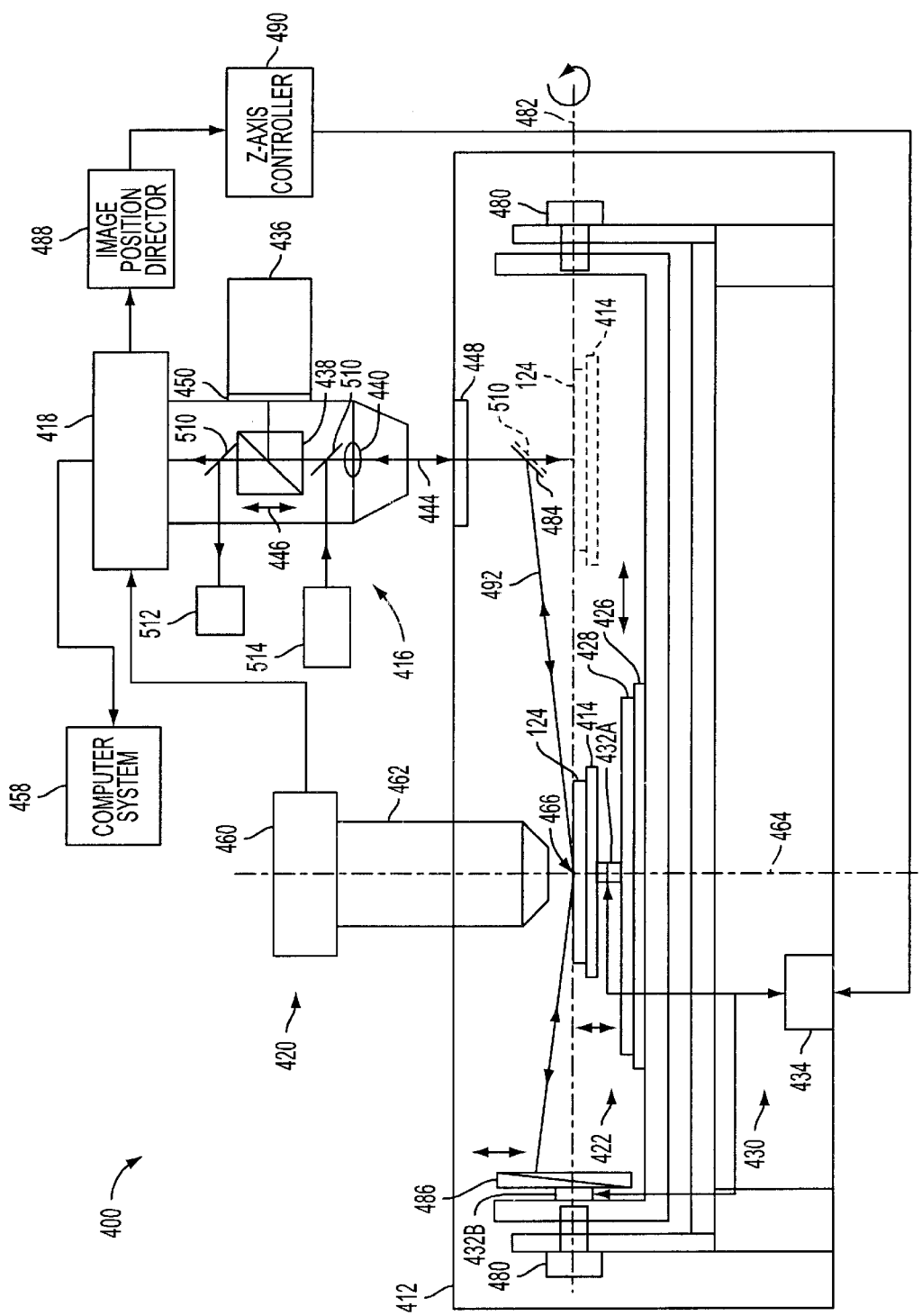
FIG. 4 is a side elevational view of a wafer inspection system constructed in accordance with another embodiment of the present invention.

FIG. 4 illustrates a wafer review system 400 constructed according to an alternative embodiment of the present invention. The wafer review system 400 of FIG. 4 includes most of the components of the system illustrated in FIG. 1, and therefore, such components will not be discussed in great detail. The wafer review system 400 of FIG. 4 differs from that of FIG. 1 in that it includes an active optical focusing system that automatically aligns the surface of the semiconductor wafer 124 with the optical axis 464 of the SEM 420. Further, the wafer review system 400 includes a pivoting mechanism 480 for rotating the stage 414 about a rotational axis 482. Accordingly, the wafer review system 400 of the present invention is capable of viewing the semiconductor wafer 124 at various angular inclinations. Alternatively, the electron column 420 can be tilted, as described in U.S. Pat. No. 5,329,125.

Referring to FIG. 4, the wafer review system 400 includes a vacuum chamber 412, a stage 414, an optical microscope 416, an imaging unit 418, a particle beam imaging system 420, and a translation system 422. The stage 414 is configured as a platform upon which the semiconductor wafer 124 may be placed. The stage 414 includes a first and second motorized base 426, 428 for adjusting the position of the semiconductor wafer 124 along, for example, an X-Y plane. The wafer review system 400 includes at least one vertical displacement unit 430 for changing the vertical position of the stage 414. Each vertical displacement unit 430 includes, for example, a lift 432A that is operated by a motor or piezo 434. As previously stated with respect to FIG. 1, the vertical displacement unit 430 assists in focusing the image of the semiconductor wafer 124 when viewed by the optical microscope 416 or the SEM 420, but may be replaced by other known focusing mechanisms.

The optical microscope 416 includes an illumination source 436, a semi-reflective mirror 438, a lens 440, and a deflection mirror (not shown). The illumination source 436 is, again, capable of producing a beam 444 of fixed or variable spot size. Similar to the embodiment of FIG. 1, a beam expander can be used to increase the spot size of the beam. The semi-reflective mirror 438 is positioned such that the beam output by the illumination source 436 strikes the surface thereof and is reflected along an illumination path 446 that is substantially perpendicular to the X-Y plane.

The illumination source 436 can be provided with a light field selector 450 that allows selection of various light fields such as, for example, bright field illumination, dark field illumination, or both. For purposes of illustration, only one beam 444 is shown. As previously stated, when bright field illumination is used, a beam 444 reflects from the semi-reflective mirror 438 and passes through the lens 440, where it is focused on the surface of the semiconductor wafer 124.

During bright field illumination, the beam 444 strikes the surface of the semiconductor wafer 124 and is reflected back toward the lens along the illumination path 446. The reflected beam passes through the semi-reflective mirror 438 and is received by an imaging unit 418 such as, for example, a CCD. The imaging unit 418 collects the beam 444 and generates a bright field image representative of the selected portion of the semiconductor wafer 124. As should be apparent, dark field illumination operates in the identical manner described with respect to FIG. 1.

The imaging unit 418 can be configured to include filters (not shown), corresponding to the filters used in the light field selector 450, for developing the images. For example, positive and negative polarizing filters (not shown) can be used to develop bright field and dark field images. Further, as previously stated, a color CCD can be used. A computer system 458 can also be coupled to the imaging unit 418 for automatically examining defects detected on the selected portion of the semiconductor wafer 124, and designating a specific defect class for the defect.

The wafer review system 400 also includes a particle beam imaging system 420 (i.e., an SEM). The SEM 420 includes an electron gun 460, and an electron optical column 462 having, for example, a low chromatic conical objective lens of approximately 60° (not shown). The electron gun 460 and the electron optical column 462 form a beam of electrons. The beam of electrons is directed along an electron beam axis 464 and converged to a focal point 466.

The focusing system includes a focusing minor 484, a reflecting mirror 486, an image position detector 488, and a Z-axis controller 490. The focusing system also utilizes the illumination source 436 for directing a focusing beam 492 at the focusing mirror 484. As illustrated in FIG. 4, the focusing mirror 484 is positioned along the illumination path 446, and oriented so as to direct the focusing beam 492 toward the focal point 466 of the SEM 420. The focusing mirror 484 can be configured such that it is moveable from the position illustrated in FIG. 4. Specifically, during examination of the semiconductor wafer 124 using the optical microscope, the focusing mirror 484 is moved so that the beam 444 from the illumination source 436 can be directed onto the surface of the semiconductor wafer 124. When the semiconductor wafer 124 is moved for examination by the SEM 420, the focusing mirror 484 is automatically positioned as illustrated in FIG. 4. Various other configurations can also be used to facilitate the use of the focusing mirror 484.

The reflecting mirror 486 is configured and positioned such that its center of curvature is at the focal point 466 of the SEM 420. When the focusing beam 492 passes through the focal point 466 of the SEM 420, it strikes the surface of the semiconductor wafer 124 at a first incident point. The focusing beam 492 is then directed to the reflecting mirror 486 and reflected back to the surface of the semiconductor wafer 124. The reflected focusing beam 492 strikes the surface of the semiconductor wafer 124 at a second incident point that is in the proximity of the first incident point. The focusing beam 492 is reflected by the focusing mirror 484 through the semi-reflective mirror 438 so that an image is resolved by the imaging unit 418. The image resolved by the imaging unit 418 is output to the image position detector 488, where it is compared to a reference frame. The reference frame can, for example, correspond to the location of the focusing beam 492 when an object is precisely positioned at the focal point 466 of the SEM 420. The image received from the imaging unit 418 is then compared to the reference frame in order to determine whether it is positioned at the focal point 466 of the SEM 420.

Figure 5:
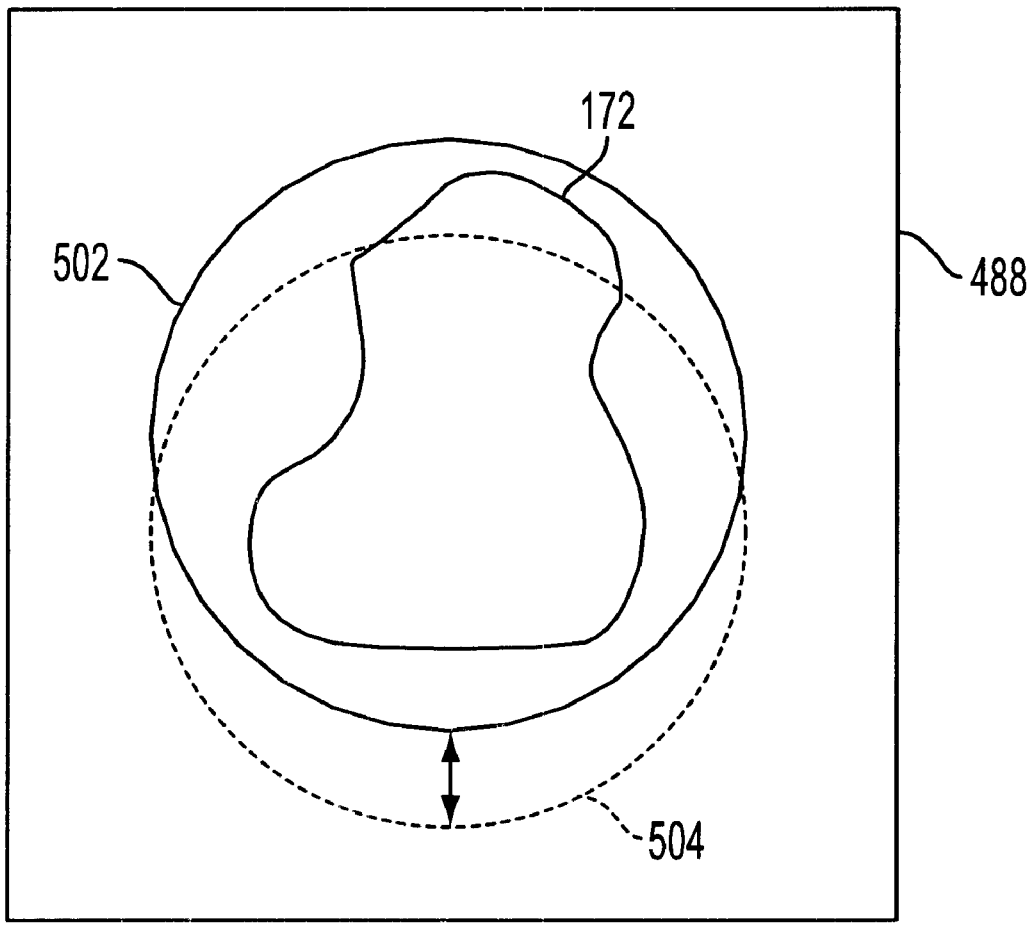
FIG. 5 is a diagram illustrating the manner in which images are focused according to an exemplary embodiment of the present invention.

FIG. 5 illustrates the manner in which the image position detector 482 actively focuses the wafer review system 400 according to an exemplary embodiment of the present invention. The image position detector 488 receives a focusing image 502 corresponding to a portion of the semiconductor wafer 124, from the imaging unit 418. The focusing image 502 is superimposed over a reference frame 504 of the image position detector 488. The image position detector 488 then determines if there is a difference between, for example, the edge of the focusing image 502 and the reference frame 504. This difference corresponds to a distance between the surface of the semiconductor wafer 124 and the focal point 466 of the SEM 420. If the focusing image 502 is aligned with the reference frame 504, then the semiconductor wafer 124 is precisely positioned at the focal point 466 of the SEM 420.

The distance between the focusing image 502 and the reference frame 504 corresponds to a focus differential that is transmitted to the Z axis controller 490. The Z axis controller 490 utilizes the focus differential to generate control voltages that operate the motors 434 of the vertical displacement unit 430 to adjust the position of the semiconductor wafer 124 and the reflecting mirror 486. This process is repeated until the image position detector 488 determines that the focusing image 502 received from the imaging unit 418 is properly aligned with the reference frame 504. According to such an embodiment, the number of times that the selected portion of the semiconductor wafer 124 must be resolved by the SEM 420 in order to generate a focused image is greatly reduced.

During normal operation, the semiconductor wafer 124 is adjusted using the focusing system until it is determined that the surface thereof is in proper alignment with the focal point 466 of the SEM 420. The selected portion of the semiconductor wafer 124 is the examined using the SEM 420, and finer focusing adjustments are made. According to the embodiment of the invention disclosed in FIG. 4, an auxiliary lift 432B is also provided to move the reflecting mirror 486 along the Z-axis. The auxiliary lift 432B can be part of the vertical displacement unit 430 and controllable by the motor 434. According to such an embodiment, operation of the auxiliary lift 432B is precisely synchronized with lift 432A so that the center of curvature of the reflecting mirror 486 is always at the focal point 466 of the SEM 420.

According to an alternative embodiment of the present invention, the illumination source 436 can be used solely for generating bright field and/or dark field illumination for examination of defects by the optical microscope. A laser 514 is subsequently provided to produce a coherent beam that will be used as the focusing beam 492. Such an embodiment elimininates the need for the focusing mirror 484. Instead, a plurality of beam splitters 510 are used direct the focusing beam 492 toward the surface of the semiconductor wafer 124. The beam splitters 510 are configured to reflect focusing beam 492 generated by the laser 514, while allowing the beam 444 from the illumination device 436 to pass therethrough. An auto-focus sensor 512 can also be provided to receive the reflected focusing beam 492 and determine if the selected portion of the semiconductor wafer 124 is positioned at the focal point 466 of the SEM 420. The auto-focus sensor 512 can be configured to output an image to the imaging unit 418, the image position detector 488, or both, in order to control operation of the vertical displacement system 430. Alternatively, the vertical displacement system 430 can be configured to the position of the stage 414 to predetermined elevation points along the Z-axis. The auto-focus sensor 512 can then be configured to examine an image of the defect at each predetermined elevation point, and select the image that is best focused for output to the imaging unit 418.

During normal operation, the semiconductor wafer 124 is adjusted using the focusing system until it is determined that the surface thereof is in proper alignment with the focal point 466 of the SEM 420. The selected portion of the semiconductor wafer 124 is the examined using the SEM 420, and finer focusing adjustments are made. According to the embodiment of the invention disclosed in FIG. 4, an auxiliary lift 432B is also provided to move the reflecting mirror 486 along the Z-axis. The auxiliary lift 432B can be part of the vertical displacement unit 430 and controllable by the motor 434. According to such an embodiment, operation of the auxiliary lift 432B is precisely synchronized with lift 432A so that the center of curvature of the reflecting mirror 486 is always at the focal point 466 of the SEM 420.

According to an alternative embodiment of the present invention, the illumination source 436 can be used solely for generating bright field and/or dark field illumination for examination of defects by the optical microscope. A laser 514 is subsequently provided to produce a coherent beam that will be used as the focusing beam 492. Such an embodiment eliminates the need for the focusing mirror 484. Instead, a beam splitter 510 is used to direct the focusing beam 492 toward the surface of the semiconductor wafer 124. The beam splitter 510 is configured to reflect the focusing beam 492 generated by the laser 514, while allowing the beam 444 from the illumination device 436 to pass therethrough. An auto-focus sensor 512 can also be provided to receive the reflected focusing beam 492 and determine if the selected portion of the semiconductor wafer 124 is positioned at the focal point 466 of the SEM 420. The auto-focus sensor 512 can be configured to output an image to the imaging unit 418, the image position detector 488, or both, in order to control operation of the vertical displacement system 430. Alternatively, the vertical displacement system 430 can be configured to adjust the position of the stage 414 to predetermined elevation points along the Z-axis. The auto-focus sensor 512 can then examine an image of the defect at each predetermined elevation point, and select the image that is best focused for output to the imaging unit 418.

Figure 6:
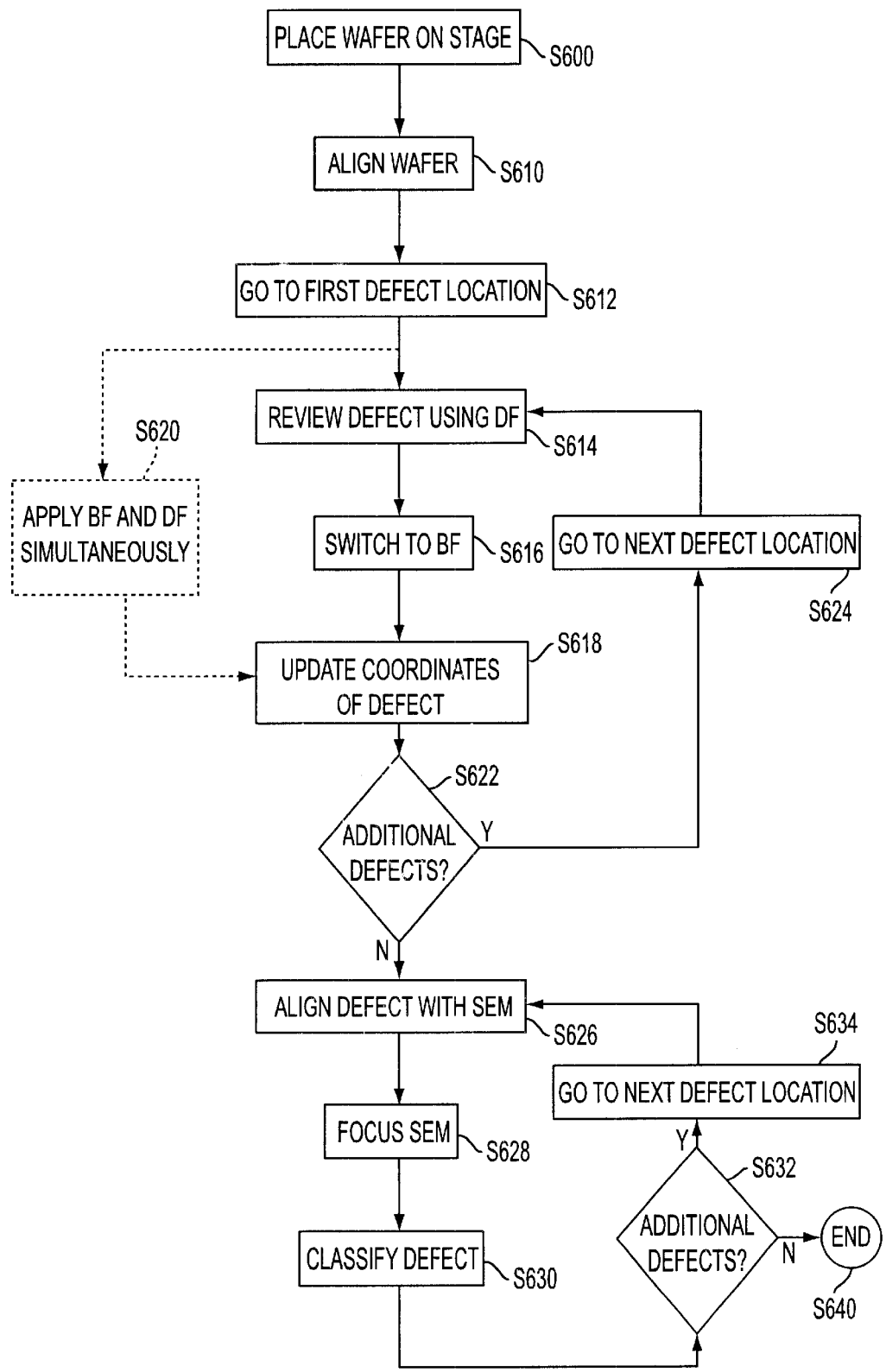
FIG. 6 is a flow chart illustrating the steps performed during inspection of the semiconductor wafer.

FIG. 6 is a flow chart illustrating the steps performed during examination of the semiconductor wafer 124 using a wafer review system constructed in accordance with the present invention. At step S600, the semiconductor wafer is placed on the stage and appropriately mounted. At step S610, the semiconductor wafer is aligned with the coordinate system of the wafer review system. As is well known in the art, such an alignment can be done using a conventional pre-aligner and/or other conventional alignment mechanisms. At step S612, the first defect location retrieved from the wafer defect map is translated to the coordinate system of the wafer review system 400 (i.e., stage coordinates). The first and second motorized bases are used to position the wafer so that the selected defect can be identified by the optical microscope.

At step S614, the defect is redetected by the wafer review system. Specifically, the defect is examined by the optical microscope using a dark field illumination, or whatever illumination type was used by the inspection tool used to generate the wafer defect map. At step S616, the light field selector is used to switch from dark field illumination to bright field illumination. At step S618, the coordinates for the defect are updated using the stage coordinates. As indicated using phantom lines, the defect can also be reviewed using both dark field and bright field illumination at step S620. As previously stated, such a review can be facilitated using various types of filters such as colored or polarizing filters. At step S622, it is determined if there are additional defects to be examined. If there are additional defects, then the stage is positioned for examination of the next defect at step S624. Control then returns to step S614. If there are no additional defects, then control passes to step S626.

At step S626, the location of the defect is aligned with the SEM. This is accomplished by using the stage coordinates to move the first and second motorized bases so that the defect will be approximately aligned with the optical axis of the SEM. If necessary, the height of the stage can be adjusted at step S628 in order to focus the image of the semiconductor wafer when viewed using the SEM. Depending on the specific embodiment of the present invention, an automatic focusing system can be used to adjust the position of the stage. If such is the case, then control passes to control block 1 wherein the height of the stage is automatically adjusted.

At step S630, the defect is classified. This step corresponds to the use of a computer system to examine the defect, compare it to predetermined defect types, and classify the defect. If the defect is clear in the SEM-based image, the classification can be performed using the SEM-based image exclusively. However, if it is insufficiently clear for classification, the optical image can be used to perform or enhance the classification. The optical image can be obtained either at step 616, or after step 626 when it was determined that classification using SEM-based image only is insufficient. At step S632, it is determined if there are any additional defects remaining to be examined. If there are additional defects, then the stage is moved so that the semiconductor wafer is positioned beneath the SEM at the location of the next defect at step S634, and control returns to step S626. If, however there are no additional defects than the review process is terminated at step S640.

The system according to the present invention can also be used to rapidly eliminate the systematic errors of the inspection system from the defect map. Specifically, the number of defects redetected is counted at step S622. When that number reaches a predetermined number, say 5, the coordinate updates of the redetected defects are examined to find common changes. For example, if it is determined that all coordinates have been corrected for a particular rotation, alpha and translation dx, dy, then this is attributed to systematic error and the coordinates of all the defects in the particular defect map are corrected for that rotation error. The rotation and translation offsets may be stored and be used again for a wafer that was inspected with the same inspection tool. Inspection tool ID is part of the information transferred to the review tool and thus a measured systematic error can be associated with a specific inspection tool.

Figure 7:
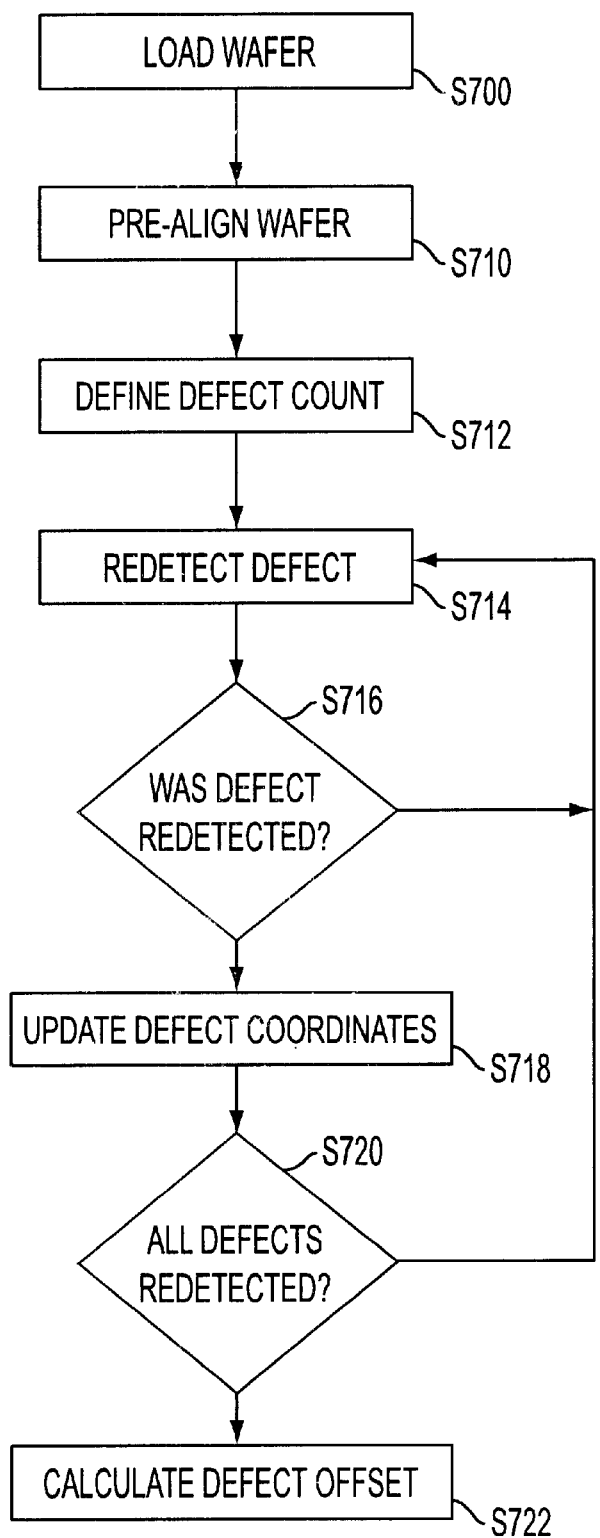
FIG. 7 is a flow chart illustrating the steps performed while focusing the semiconductor wafer for viewing by the SEM.

FIG. 7 is a flow chart illustrating the manner in which defect offsets generated by the inspection tool are corrected by the wafer review system of the present invention. At step S700, the semiconductor wafer is placed on the stage, and data corresponding to the location of defects (i.e., the defect map) is transmitted to the wafer review system. As previously stated, the defect map contains the coordinates of potential defects previously identified by the inspection tool. The data transferred to the wafer inspection system also includes an inspection tool ID that identifies the inspection tool used to generate the defect map for the semiconductor wafer.

At step S710, the semiconductor wafer is pre-aligned with the coordinate axes of the wafer review system. The number of defects that will be used to determine the defect offset (i.e., the defect count) is defined at step S712. At step S714, the wafer review system attempts to redetect the first defect (i.e., using the optical microscope, for example). At step S716, it is determined whether the defect was successfully redetected. If the defect was not successfully redetected, then control returns to step S714, where additional attempts, such as, for example, combined bright field and dark field illumination, are applied to redetect the defect. If the defect is successfully redetected, then control passes to step S718, where the defect coordinates are updated relative to the coordinates of the wafer review system.

At step S720, it is determined if a number of defects corresponding to the defect count (selected at step S712) has been redetected. If the number of redetected defects is less than the defect count, then control returns to step S714, where the next defect in the defect map is redetected. If the number of redetected defects is equal to the defect count, then control passes to step S722. At step S722, defect offsets are calculated for the semiconductor wafer.

As previously stated, the defect offsets are representative of rotational and transnational displacements attributed to the systematic errors of the inspection tool. According to such an embodiment, once the defect offsets have been calculated, such offsets can be applied to correct systematic errors in all the remaining defect locations for the semiconductor wafer. Specifically, corrections for the systematic errors can be maintained in a memory, such as in computer 158, together with the corresponding inspection system ID. Further, if the same inspection tool is used to generate defect maps for multiple semiconductor wafers, then the same defect offsets can be retrieved from the memory and be applied to correct systematic errors in all of the semiconductor wafers having defect map with the same system ID. According to the exemplary embodiment of the present invention, the wafer review system can examine the inspection tool ID contained in the transferred data in order to determine which specific inspection tool was used to generate the defect map for the semiconductor wafer currently being examined. If the inspection tool ID matches the inspection tool ID of the inspection tool used to generate the defect map from which the defect offsets were calculated, then the same defect offsets can be applied to correct systematic errors contained in the current semiconductor wafer. Such an embodiment has an advantage of minimizing the number of times defect offsets must be calculated for an individual semiconductor wafer, or multiple semiconductor wafers examined by the same inspection tool.

Figure 8:
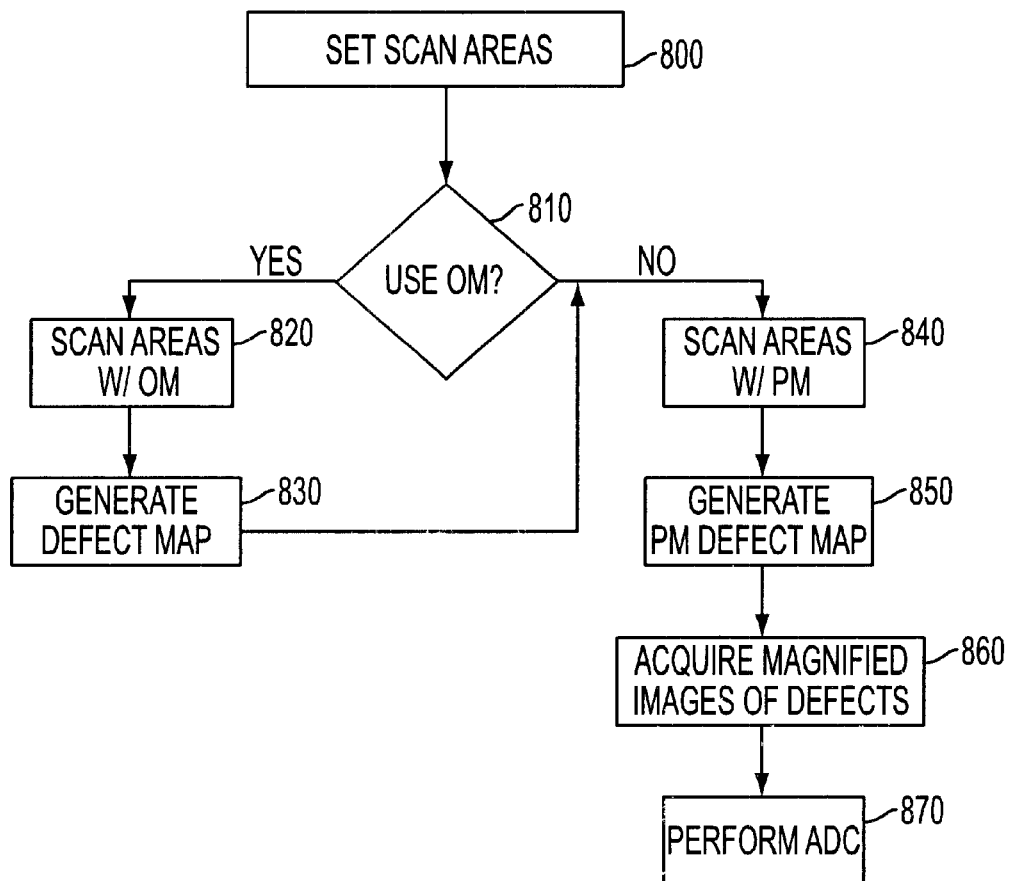
FIG. 8 is a flow chart illustrating the steps performed in deciding on using a optical microscope or particle microscope to scan the substrate.

FIG. 8 is a flow chart of another particular method of the present invention. Specifically, according to this embodiment, the system of the invention can be used to inspect substrates for defects. That is, it is well known that certain process defects may not be detectable by current optical systems. Therefore, systems such as the SEMSpec, marketed by KLA of San Jose, Calif., use electron beam to scan the entire wafer to detect defect that cannot be detected using optical inspection systems. The SEMSpec system is described in U.S. Pat. Nos. 5,578,821 and 5,502,306. However, the SEMspec is a very expensive and very slow system, which can scan only one or two wafers per day (as opposed to 30–60 wafers per hour achieved by optical systems). The embodiment depicted in FIG. 8 provides a much faster e-beam based inspection system at a lower cost and faster scan rate than are currently available.

In essence, the embodiment of FIG. 8 uses intelligent selection to perform e-beam based scanning of the substrate and detect defects. That is, circuit designers generally know where are the areas on the circuit that are pronged to have defects thereupon. For example, areas having dense pattern, areas having many contact holes, areas having many conduction lines close together with the possibility of having bridging of the lines, etc. Using this information, the designer can intelligently select areas of the circuit, i.e., on the wafer, that should be inspected carefully. Using this information, the designer can set coordinates for the areas to be scanned, as exemplified in step 800. In the preferred embodiment, this is done by writing an "artificial" or "synthetic" defect map. That is, the areas to be scanned are defined by writing an artificial defect map instructing the system to inspect those areas as suspected of having defects thereupon.

Once the system receives the set scan areas, or the artificial defect map, it have the option of running first the optical microscope, i.e., choosing path YES at junction 810, or going directly to scanning with the particle microscope, i.e., choosing NO at junction 810 as seen in FIG. 8. If path YES is chosen, the optical microscope 116 is used to scan the substrate according to the defect map (step 820). Then, a defect map is created by the optical microscope, designating any found defects (step 830). Thereafter, or if path NO is chosen at junction 810, the set scan areas are scanned by the particle microscope at step 840. Using a die-to-die comparison on the images obtained by the particle microscope, a new defect map is generated by the computer 158 (step 850). The die-to-die comparison can be done, for example, according to the method currently being performed by the SEMVision, i.e., for each designated location, a corresponding location on an adjacent die is imaged, and the images are compared to detect discrepancies. It should be appreciated that this latter defect map is very accurate since it is based on the high resolution of the particle beam microscope. The process can stop here, if all that is required is a defect map.

If further information about the found defects is sought, the process can continue to step 860, wherein magnified images of each defect are obtained, using the particle microscope. Then, at step 870, computer 158 can perform the automatic defect classification (ADC) as described above.

Although the present invention has been described with respect to examination of defects on a semiconductor wafer, it should be appreciated that such an arrangement can be easily used in conjunction with various other materials and surfaces. For example, the present invention can be used to examine photomasks, magnetic disks, optical disks, mirrors, etc. Furthermore, the present invention can be used to examine semiconductor materials during various stages of the manufacturing process. Specifically, the present invention is equally applicable to examination of either patterned or unpatterned semiconductor wafers.

The present invention advantageously provides an ability to quickly and accurately redetect and classify defects on (or near) the surface of an object such as a semiconductor wafer. This is accomplished using a material review system includes both an optical microscope and an SEM. The optical microscope is configured such that it is capable of generating an illumination field similar to the illumination field used generate a defect map for the semiconductor wafer. Such a configuration allows accurate and efficient redetection of defects. The system includes a translation system for moving the semiconductor wafer for alignment with the SEM once all the defects have been redetected by the optical microscope. The SEM provides high resolution magnification of the defect so that a review and classification can be made. The present invention can also be provided with an active optical focusing system that automatically adjusts the stage in order to focus the SEM on the defect. Furthermore, a pivoting system can be provided for rotating the stage about a rotational axis and viewing the defect from different perspectives.

One advantage of such an arrangement is the ability to accurately redetect defects using the optical microscope. Additionally, once a defect is redetected, it can be accurately positioned for examination by the SEM. Hence, the need to randomly search a large area using the limited field of view of the SEM is eliminated. Moreover, the system can calculate systematic errors of a particular inspection system and automatically apply corrections to defect map received from such a system. Another advantage of the present invention is the ability to classify defects that cannot be imaged by the SEM, hence minimizing the number of defects that are not classified during the review process.

While this invention has been described in connection with what is presently considered to be the most practical and preferred embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for reviewing defects on an object surface, based on a previously generated defect map, said apparatus comprising:

a stage for receiving said object thereon;

an optical microscope comprising an illumination source providing a light beam, said optical microscope directing said light beam toward a selected portion of said object surface based on information contained in the defect map;

a light sensor coupled to said optical microscope for detecting defects illuminated by said light beam;

a particle beam imaging system for converging a beam of particles to a focal point along a prescribed axis; and a translation system positioning said redetected defect proximate said focal point;

wherein said redetected defect can be subsequently reviewed using said particle beam imaging system.

2. The apparatus of claim 1, wherein said translation system includes:

a first motorized base for moving said stage along a first axis; and a second motorized base for moving said stage along a second axis;

wherein said first and second axes are substantially perpendicular to each other, and define a plane.

3. The apparatus of claim 1, wherein said microscope is configurable for operation in bright field mode, dark field mode, and a combination of both bright field and dark field mode.

4. The apparatus of claim 1, further comprising a computer system for classifying defects reviewed by said particle beam system.

5. The apparatus of claim 4, wherein said computer system is configured to further classify defects imaged by said microscope.

6. The apparatus of claim 1, wherein said illumination source comprises a laser.

7. The apparatus of claim 3, further comprising:

a mode selector operatively coupled to said microscope for selectively forming a prescribed illumination type to generate said dark and bright field modes.

8. The apparatus of claim 7, wherein said selector comprises a filter insertable into to illumination path of said microscope.

9. The apparatus of claim 7, wherein said illumination source comprises a lamp light source providing bright field illumination and a laser source providing dark field illumination.

10. The apparatus of claim 9, wherein said dark field illumination approaches said object surface at an oblique angle.

11. The apparatus of claim 1, further comprising a second illumination sources for directing an auxiliary beam of light toward said object surface at an oblique angle.

12. The apparatus of claim 1, further comprising a focusing system for automatically maintaining said object surface at a focal point of said particle imaging system.

13. The apparatus of claim 12, wherein said focusing system includes:

a coherent light source for generating a focusing beam;

a focusing mirror for directing said focusing beam toward said object surface through said focal point, said focusing beam striking said object surface at a first incident point;

a reflecting mirror for reflecting said focusing beam back on to said object surface at a second incident point, said second incident point being in the proximity of said first incident point; and an image alignment system for detecting a distance between said object surface and said focal point, and vertically adjusting said stage to align said object surface with said focal point.

14. The apparatus of claim 13, further comprising a selection mechanism selectively activating said focusing system when said particle beam imaging system images a defect, and deactivating said focusing system when said microscope is in operation.

15. The apparatus of claim 14, wherein said selection mechanism comprises a mirror insertable in illumination path of said microscope.

16. The apparatus of claim 14, wherein said selection mechanism comprises a diachroic mirror placed in illumination path of said microscope.

17. The apparatus of claim 1, wherein said sensor is a color CCD.

18. The apparatus of claim 3, wherein illumination of said bright and dark field mode is color coded, and wherein said sensor is a color CCD.

19. The apparatus of claim 1, further comprising an error calculator receiving defect coordinates from said defect map and stage coordinates from said microscope and calculating reporting error in said defect map.

20. The apparatus of claim 19, further comprising an error memory storing said reporting error in correlation to a system ID, and applying said reporting error to any defect map having said system ID.

21. A method of reviewing defects on an object surface, based on a previously generated defect map, the method comprising the steps:

viewing selected portions of the object surface with an optical microscope, based on coordinates from a defect map, to redetect the defects;

determining stage coordinates corresponding to the location of the redetected defects;

calculating reporting error from said defect map and said stage coordinates;

moving the object surface to position the redetected defects proximate a focal point of a particle beam imaging system; and reviewing the redetected defects using the particle beam imaging system.

22. The method of claim 21, wherein the step of viewing selected portions of the object surface with an optical microscope comprises illuminating the object surface with dark field illumination.

23. The method of claim 22, further comprising the step of obtaining magnified optical images of defects by operating the microscope in a bright field mode.

24. The method of claim 21, wherein the step of viewing comprises simultaneously applying bright field and dark field illumination on the selected portion of the object surface to produce a composite bright and dark field images of the defect.

25. A method of inspecting a surface of a wafer for defects using electron-beam microscope, comprising:

generating a list of designated areas on the wafer to be inspected;

providing the list of designated areas to the microscope to perform scanning with electron beam of the designated areas;

performing a die-to-die inspection to detect defects in the designated areas; and, construct an e-based defect map.

26. The method of claim 25, wherein said list of designated areas in constructed in the form of an artificial defect map.

* * * * *